(12) United States Patent
Tsuji et al.

(10) Patent No.: US 6,211,388 B1
(45) Date of Patent: Apr. 3, 2001

(54) METHOD FOR PRODUCING PROPYLENE OXIDE

(75) Inventors: Junpei Tsuji, Ichihara; Jun Yamamoto, Sodegaura, both of (JP); Avelino Corma Canos; Fernando Rey Garcia, both of Valencia (ES)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/414,555

(22) Filed: Oct. 8, 1999

(30) Foreign Application Priority Data

Oct. 14, 1998 (ES) .................................................... 9802135

(51) Int. Cl.$^7$ ................................................ C07D 301/12
(52) U.S. Cl. ............................................................ 549/519
(58) Field of Search ................................... 549/510, 529, 549/519

(56) References Cited

U.S. PATENT DOCUMENTS

| | | | |
|---|---|---|---|
| 4,367,342 | 1/1983 | Wulff et al. | 549/529 |
| 5,783,167 | 7/1998 | Corma Canos et al. | 423/701 |
| 6,011,162 | * 1/2000 | Han et al. | 549/529 |

FOREIGN PATENT DOCUMENTS 0 655 278    5/1995   (EP) .
7-300312    11/1995   (JP) .

* cited by examiner

Primary Examiner—Deborah C. Lambkin
Assistant Examiner—Sonya Wright
(74) Attorney, Agent, or Firm—Sughrue, Mion, Zinn, Macpeak & Seas, PLLC

(57) ABSTRACT

A method for producing propylene oxide by reacting propylene with ethylbenzene hydroperoxide, wherein the reaction is conducted in the presence of a catalyst comprising a titanium-containing silicon oxide and satisfying all of the following conditions (1) to (6):

(1) there is at least one peak showing a interplanar spacing (d) larger than 18 Å in X-ray diffraction;
(2) an average pore size is 10 Å or more;
(3) a pore size of 90% or more of the total pore volume is 5 to 200 Å;
(4) a specific pore volume is 0.2 cm$^3$/g or more;
(5) a quaternary ammonium ion represented by the following general formula (I) is used as a template and then said template is removed by calcination operation:

$$[NR^1R^2R^3R^4]^+ \qquad (I)$$

wherein $R^1$ represents a linear or branched hydrocarbon chain having 2 to 36 carbon atoms, and $R^2$ to $R^4$ represent an alkyl group having 1 to 6 carbon atoms; and (6) The catalyst has been subjected to silylation treatment.

9 Claims, 1 Drawing Sheet

METHOD FOR PRODUCING PROPYLENE OXIDE

BACKGROUND OF THE INVENTION

1. Field of the Invention

The present invention relates to a method for producing propylene oxide. More particularly, the present invention relates to a method for producing propylene oxide by reacting propylene with ethylbenzene hydroperoxide to obtain propylene oxide in high yield and high selectivity.

2. Description of the Related Art

It is known that propylene oxide can be produced by reacting propylene with ethylbenzene hydroperoxide. For example, U.S. Pat. No. 4,367,342 discloses a method using a titanium supported silica catalyst. However, it is not necessarily to produce propylene oxide in high yield and high selectivity in the conventional methods.

SUMMARY OF THE INVENTION

Under these circumstances, an object of the present invention is to provide a method for producing propylene oxide by reacting propylene with ethylbenzene hydroperoxide to obtain propylene oxide in high yield and high selectivity.

Namely, the present invention relates to a method for producing propylene oxide by reacting propylene with ethylbenzene hydroperoxide, wherein said reaction is conducted in the presence of a catalyst comprising a titanium-containing silicon oxide and satisfying all of the following conditions (1) to (5):

(1): There is at least one peak showing a interplanar spacing (d) larger than 18Å in X-ray diffraction.

(2): An average pore size is 10 Å or more.

(3): A pore size of 90% or more of the total pore volume is 5 to 200 Å.

(4): A specific pore volume is 0.2cm$^3$/g or more.

(5): A quaternary ammonium ion represented by the following general formula (I) is used as a template and then said template is removed by calcination operation;

(wherein, $R^1$ represents a linear or branched hydrocarbon chain having 2 to 36 carbon atoms, and $R^2$ to $R^4$ represent an alkyl group having 1 to 6 carbon atoms.).

DETAILED DESCRIPTION OF THE PREFERRED EMBODIMENTS

Figure 1:
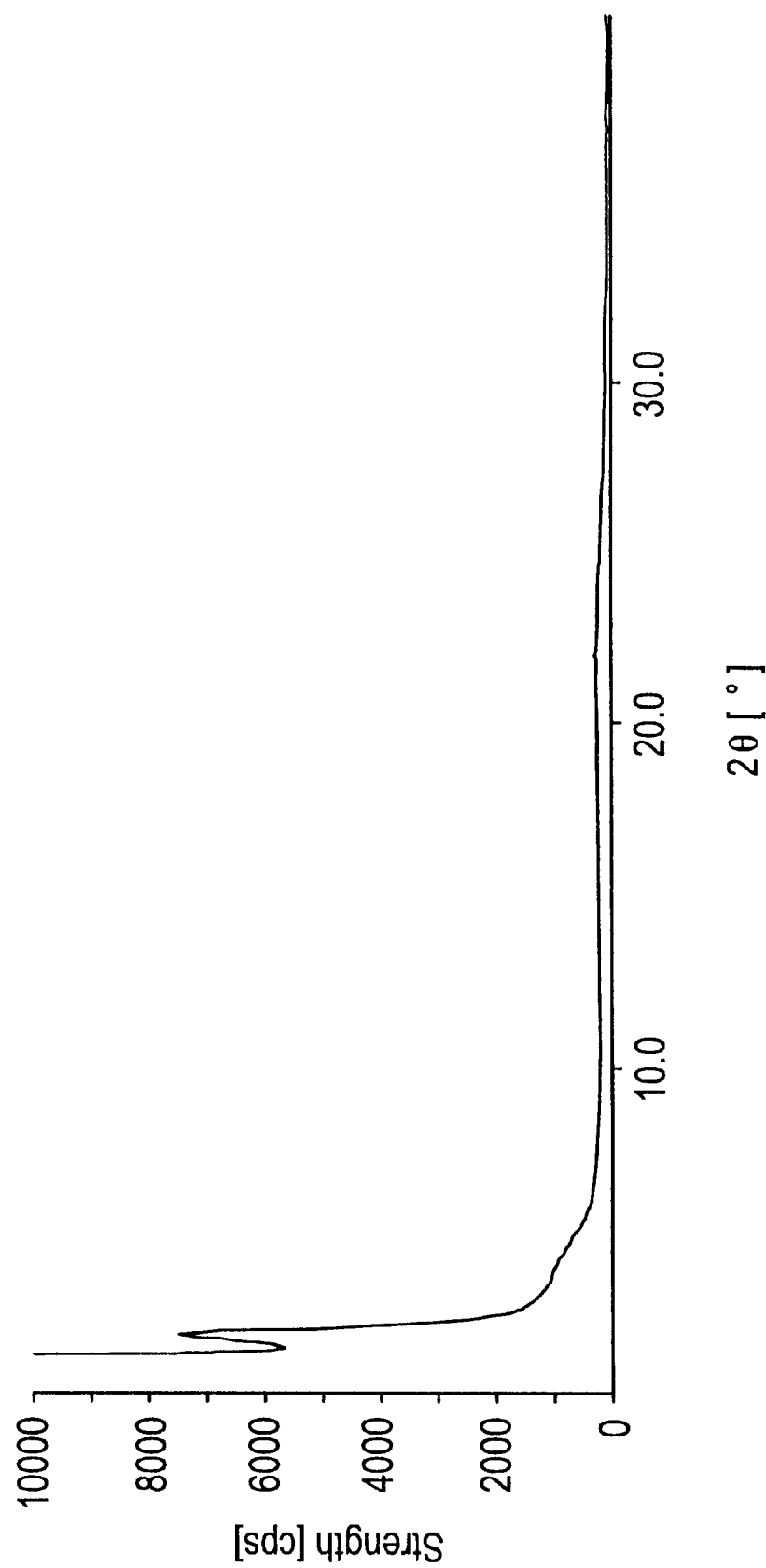
FIG. 1 is a X-ray diffraction chart of a catalyst in Example 1.

The catalyst used in the present invention is a catalyst comprising a titanium-containing silicon oxide and satisfying all of the following conditions (1) to (5). The effect of the present invention can be fully accomplished by using said catalyst.

The condition (1) shows that the catalyst has at least one peak showing a interplanar spacing (d) larger than 18 Å in X-ray diffraction (XRD). The peak showing interplanar spacing (d) as herein referred to means a peak derived from crystallinity and regularity of solid, and a broad peak derived from amorphous part may exist. When a peak showing interplanar spacing (d) larger than 18 Å exists in X-ray diffraction, it is preferable that this peak is a part of peak group showing structure of hexagonal system.

The condition (2) shows that an average pore size of the catalyst is 10 Å or more.

The condition (3) shows that a pore size of 90% or more of the total pore volume of the catalyst is 5 to 200 Å.

The condition (4) shows that a specific pore volume of the catalyst is 0.2cm$^3$/g or more. The specific pore volume means pore volume per 1g of the catalyst.

The properties of the catalyst described in the above-described conditions (2) to (4) can be measured by usual methods utilizing physical adsorption of a gas such as nitrogen, argon and the like.

The condition (5) shows that the catalyst is obtained by using a quaternary ammonium ion represented by the following general formula (I) as a template and then removing said template by calcination operation;

(wherein, $R^1$ represents a linear or branched hydrocarbon chain having 2 to 36 carbon atoms, and $R^2$ to $R^4$ represent an alkyl group having 1 to 6 carbon atoms.).

$R^1$ represents a linear or branched hydrocarbon chain having 2 to 36 carbon atoms, preferably 10 to 18 carbon atoms. $R^2$ to $R^4$ represent an alkyl group having 1 to 6 carbon atoms, and preferably each of $R^2$ to $R^4$ represents a methyl group.

Specific examples of the quaternary ammonium ion represented by the general formula (I) include cations such as hexadecyltrimethylammonium, dodecyltrimethylammonium, benzyltrimethylammonium, dimethyldidodecylammonium, hexadecylpyridinium, hexadecyltrimethylphosphonium and the like.

Preferable specific embodiments in which the catalyst of the present invention is obtained are as follows.

A silica source, a titanium source and a quaternary ammonium ion as a template are mixed and stirred in liquid condition. When a reagent to be used is solid, it may be dissolved in a solvent and used as a solution.

Examples of the silica source include amorphous silica alkoxysilane such as tetramethylorthosilicate, tetraethyl orthosilicate, tetrapropyl orthosilicate and the like.

Examples of the titanium source include titanium alkoxides such as tetramethyl titanate, tetraethyl titanate, tetrapropyl titanate, tetraisopropyl titanate, tetrabutyl titanate, tetraisobutyl titanate, tetra-2-ethylhexyltitanate, tetraoctadecyltitanate, and titanium (IV) oxyacetylacetonate, titanium (IV) diisopropoxybisacetyl acetonate and the like, and titanium halides such as titanium tetrachloride, titanium tetrabromide, titanium tetraiodide and the like.

Examples of the solvent include water and alcohol such as methanol, ethanol, n-propanol, 2-propanol, n-butanol, sec-butanol, t-butanol, vinyl alcohol, allyl alcohol, cyclohexanol, benzyl alcohol and the like, and diols, or a mixture thereof, and the like.

The amount used of the titanium source based on the silica source is from $10^{-5}$ to 1, preferably from 0.00008 to 0.4 in terms of molar ratio. The amount used of the quarternary ammonium ion based on the total amount of these silica source and titanium source is preferably from $10^{-2}$ to 2 in terms of molar ratio.

For promoting the reaction of the silica source and the titanium source, it is preferable to impart alkalinity or acidity to the mixed solution. As the alkali source, quaternary ammonium hydroxides are preferable, and examples thereof include tetramethylammonium hydroxide, tetraethylammonium hydroxide, tetrapropylammonium hydroxide and the like. Examples of the acid include inorganic acids such as hydrochloric acid, sulfuric acid, nitric acid and the like, and organic acids such as formic acid, acetic acid, propionic acid and the like.

The mixing and stirring temperature is usually from −30 to 100° C. Solid is formed by mixing and stirring, and the solid may be aged for further growth thereof. The aging time is usually 180 hours or less, and aging temperature is usually from 0 to 200° C. When heating is required in aging, it is preferable that the mixture is transferred into a pressure vessel and heating is conducted for avoiding vaporization of the solvent. The resulted solid is filtered off and collected. The collected solid may be washed using water and solvent. The resulted solid is dried. The dried solid is calcinated, and the template is removed. The calcination temperature is usually from 400 to 800° C., and the time required is usually from 1 to 100 hours.

According to the above-described operation, the catalyst used in the present invention is obtained, and it is preferable that subsequently silylation treatment is conducted. The silylation treatment is usually conducted by contacting a catalyst after calcination with a silylation agent, and converting a hydroxyl group existing on the surface of the catalyst into a silyl group. Examples of the silylation agent include an organic silane, organic silylamine, organic silylamide and derivatives thereof, and organic silazane and other silylation agents.

Examples of the organic silane include chrolotrimethylsilane, dichlorodimethylsilane, chlorobromodimethylsilane, nitrotrimethylsilane, chlorotriethylsilane, iododimethylbutylsilane, chlorodimethylphenylsilane, chlorodimethylsilane, dimethyl n-propylchlorosilane, dimethylisopropylchlorosilane, t-butyldimethylchlorosilane, tripropylchlorosilane, dimethyloctylchlorosilane, tributylchlorosilane, trihexylchlorosilane, dimetylethylchlorosilane, dimethyloctadecylchlorosilane, n-butyldimethylchlorosilane, bromomethyldimethylchlorosilane, chloromethyldimethylchlorosilane, 3-chloropropyldimethylchlorosilane, dimethoxymethylchlorosilane, methylphenylchlorosilane, triethoxychlorosilane, dimethylphenylchlorosilane, methylphenylvinylchlorosilane, benzyldimethylchlorosilane, diphenylchlorosilane, diphenylmethylchlorosilane, diphenylvinylchlorosilane, tribenzylchlorosilane, 3-cyanopropyldimethylchlorosilane.

Examples of the organic silylamine include N-trimethylsilylimidazole, N-t-butyldimethylsilylimidazole, N-dimethylethylsilylimidazole, N-dimethyl n-propylsilylimidazole, N-dimethylisopropylsilylimidazole, N-trimethylsilyldimethylamine, N-trimethylsilyldiethylamine, N-trimethylsilylpyrrole, N-trimethylsilylpyrrolidine, N-trimethylsilylpiperidine, 1-cyanoethyl(diethylamino)dimethylsilane, pentafluorophenyldimethylsilylamine.

Examples of the organic silylamide and derivatives include N,O-bistrimethylsilylacetamide, N,O-bistrimethylsilyltrifluoroacetamide, N-trimethylsilylacetamide, N-methyl-N-trimethylsilylacetamide, N-metyl-N-trimethylsilyltrifluoroacetamide, N-methyl-N-trimethylsilylheptafluorobutylamide, N-(t-butyldimethylsilyl)-N-trifluoroacetamide, N,O-bis(diethylhydrosilyl)trifluoroacetamide.

Examples of the organic silazane include hexamethyldisilazane, heptamethyldisilazane, 1,1,3,3-tetramethyldisilazane, 1,3-bis(chloromethyl)tetramethyldisilazane, 1,3-divinyl-1,1,3,3-teteramethyldisilazane, 1,3-diphenyltetramethyldisilazane.

Examples of the other silylation agent include N-methoxy-N,O-bistrimethylsilyltrifluoroacetamide, N-methoxy-N,O-bistrimethylsilyl carbamate, N,O-bistrimethylsilyl sulfamate, trimethylsilyltrifluoromethane sulfonate, N,N'-bistrimethylsilylurea.

The preferable silylation agent is hexamethyldisilazane.

The catalyst in the present invention is preferably a catalyst having an absorption peak in the range of 960 ±5 $cm^{-1}$ in infrared absorption spectrum. This peak is considered to correspond to titanium introduced into silica skeleton.

The present invention is a method for producing propylene oxide by reacting propylene with ethylbenzene hydroperoxide in the presence of the above-mentioned catalyst.

Ethylbenzene hydroperoxide used as the raw material may be a diluted or concentrated purified product or non-purified product.

The epoxidization can be effected in liquid phase by using a solvent and/or diluting agent. The solvent and diluting agent must be liquid under the temperature and pressure in reaction, and substantially inert to the reactant and the product. The solvent may be composed of a substance existing in the hydroperoxide solution used. When ethylbenzene hydroperoxide (EBHP) is a mixture composed of EBHP and ethylbenzene which is a raw material thereof, there is no particular need to add a solvent, and this may also be used for a solvent. Further, excess amount of propylene can be used as a solvent.

The ratio to be used of propylene/ethylenebenzene hydroperoxide is usually from 0.1 to 20. The reaction temperature is usually from 0 to 200° C., and the reaction pressure is usually from 1 to 100 $kg/cm^2$.

The method of the present invention can be advantageously carried out by using a catalyst in the form of a fixed bed. In the case of a large scale of industrial operation, it is preferable to use a fixed bed. The method of the present invention can be carried out by a batchwise method, semi-continuous method or continuous method. When a solution containing a reactant is introduced through a fixed bed, a liquid mixture obtained from reaction solution contains no catalyst at all or substantially no catalyst.

EXAMPLE

Example 1

Preparation of Titanium-containing MCM41 Catalyst (Catalyst of the Present Invention)

With 87 g of water was mixed 26 g of cetyltrimethylammonium bromide and 24 g of a 25 wt % aqueous tetramethylammonium hydroxide solution, and to this mixture was added a mixture of 38 g of tetramethyl orthosilicate, 2.5g of titanium (IV) diisopropoxy bisacetylacetonate and 30g of isopropyl alcohol at room temperature. The mixture was stirred for 3 hours, then, the resulted precipitate was filtered off, and washed with water. The washing was conducted until the washing solution became neutral. The filtered white solid was dried at 70° C. for 5 hours under reduced pressure. The solid was transferred to a tubular furnace, heated at 2° C./min up to 530° C. for 1 hour under nitrogen flow. Then, nitrogen was substituted by air and calcinated for further 5 hours. This substance (5 g), hexamethyldisilazane (3.4 g) and toluene (50 g) were mixed, and the mixture was heated for 1 hour under reflux with stirring. Liquid was distilled off by filtration from the mixture. It was washed with toluene (100 g), and dried under reduced pressure (120° C., 10 mmHg, 3 hours) to obtain a catalyst. Thus obtained catalyst had a specific surface area of 1390 m²/g, an average pore size of 41Å and a pore volume of 1.4 cc/g.

Synthesis of Propylene Oxide (PO)

The above-described catalyst (2 g) and 35 wt % ethylbenzene hydroperoxide (16 g) and propylene (12 g) were charged in an autoclave equipped with a magnetic stirred, and they were reacted at 90° C. for 0.5 hours. The reaction results are shown in Table 1.

Comparative Example 1

Preparation of Titanium Supported Catalyst
(Catalyst Out of the Present Invention)

Acetylacetone (1.6 g) was added slowly to a solution of tetraisopropyl titanate (2.2 g) in isopropanol (20 ml) with stirring under nitrogen flow, then, the mixture was stirred at room temperature for 30 minutes. To a mixture of a commercially available silica gel (10 to 20 mesh, surface area 326 m²/g, average pore size 10 nm)(50 g) and isopropanol (230 ml) were added the above-described solution dropwise, then, the mixture was stirred at room temperature for 1 hour before filtration of the mixture. The solid portion was washed with isopropanol three times (total 250 ml). The solid portion was dried at 150° C. for 2 hours under air atmosphere. The solid portion was further calcined at 600° C. for 4 hours under air atmosphere. This substance (10 g), hexamethyldisilazane (4 g) and toluene (50 g) were mixed and stirred, and heated for 1 hour under reflux. Liquid was distilled off from the mixture by filtration. It was washed with toluene (100 g) and dried under reduced pressure (120° C., 10 mmHg, 3 hours) to obtain a catalyst.

Epoxidation reaction was conducted by using the above-described catalyst for 1 hour. The results are shown in Table 1.

Comparative Example 2

Epoxidation reaction was conducted in the same manner as in Comparative Example 1 except that a TS-1 catalyst manufactured by NE Chemcat Corp was used. (catalyst out of the invention)(surface area 468 m²/g, Si/Ti=50). The results are shown in Table 1.

TABLE 1

| | Example 1 | Comparative example 1 | Comparative example 2 |
|---|---|---|---|
| Catalyst properties | | | |
| X-ray diffraction | | | |
| Peak showing interplanar spacing d > 18 Å | Recognized | None | None |
| Peak showing interplanar spacing which does not satisfy d > Å | Recognized | None | Recognized |
| Average pore size Å | 41 | 138 | 15 |
| Pore distribution range Å | 5–80 | 5–200 | 5–10 |
| Specific pore volume cm³/g | 1.43 | 0.95 | 0.17 |
| Template | T-1 | Not used | T-2 |

TABLE 1-continued

| | Example 1 | Comparative example 1 | Comparative example 2 |
|---|---|---|---|
| Reaction results | | | |
| Reaction time h | 0.5 | 1.0 | 1.0 |
| EBHP conversion % | 99.2 | 94.9 | 32.2 |
| PO selectivity % | 89.2 | 89.2 | 75.6 |

*1T-1: Cetyltrimethylammonium bromide
*2T-2: Tetrapropylammonium hydroxide

As described above, according to the present invention, it can be provided that a method for producing propylene oxide by reacting propylene with ethylbenzene hydroperoxide to obtain propylene oxide in high yield and high selectivity.

What is claimed is:

1. A method for producing propylene oxide by reacting propylene with ethylbenzene hydroperoxide, wherein said reaction is conducted in the presence of a catalyst comprising a titanium-containing silicon oxide and satisfying all of the following conditions (1) to (6):

(1) there is at least one peak showing a interplanar spacing (d) larger than 18 Å in X-ray diffraction;
   (2) an average pore size is 10 Å or more;
   (3) a pore size of 90% or more of the total pore volume is 5 to 200 Å;
   (4) a specific pore volume is 0.2 cm³/g or more; and
   (5) a quaternary ammonium ion represented by the following general formula (I) is used as a template and then said template is removed by calcination operation:

$$[NR^1R^2R^3R^4]^+ \quad (I)$$

wherein $R^1$ represents a linear or branched hydrocarbon chain having 2 to 36 carbon atoms, and $R^2$ to $R^4$ represent an alkyl group having 1 to 6 carbon atoms; and (6) said catalyst has been subjected to silylation treatment.

2. The method according to claim 1, wherein the peak in X-ray diffraction is a part of peak group showing hexagonal system.

3. The method according to claim 1, wherein the catalyst has an absorption peak in the range of 960±5 cm in infrared ray absorption spectrum.

4. The method according to claim 1, wherein said silylation treatment is conducted by contacting the catalyst after calcination with a silylation agent.

5. The method according to claim 4, wherein said silylation agent is selected from the group consisting of organic silanes, organic silylamines, organic silylamides and organic silazanes.

6. The method according to claim 4, wherein said silylation agent is hexamethyldisilazane.

7. The method according to claim 1, wherein the ratio of propylene to ethylbenzene hydroperoxide is from 0.1 to 20.

8. The method according to claim 1, wherein the reaction temperature is from 0 to 200° C.

9. The method according to claim 1, wherein the reaction pressure is from 1 to 100 kg/cm².

* * * * *